US010646443B2

(12) United States Patent
Claassen-Punt et al.

(10) Patent No.: US 10,646,443 B2
(45) Date of Patent: *May 12, 2020

(54) SUSTAINED RELEASE OLANZAPINE FORMULATIONS

(71) Applicant: Teva Pharmaceuticals International GMBH, Jona (CH)

(72) Inventors: Carine Claassen-Punt, Leiden (NL); Mark Alan Smith, Elkton, MD (US); Ling Chen, Exton, PA (US); Ari Andrew Gershon, Petach Tikva (IL)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/926,076

(22) Filed: Mar. 20, 2018

(65) Prior Publication Data

US 2018/0263911 A1   Sep. 20, 2018

Related U.S. Application Data

(60) Provisional application No. 62/473,608, filed on Mar. 20, 2017.

(51) Int. Cl.

| | |
|---|---|
| *A61K 31/551* | (2006.01) |
| *A61P 25/18* | (2006.01) |
| *A61K 47/34* | (2017.01) |
| *A61K 9/14* | (2006.01) |
| *A61K 31/5513* | (2006.01) |
| *A61K 9/00* | (2006.01) |
| *A61K 9/16* | (2006.01) |

(52) U.S. Cl.
CPC ............ *A61K 9/146* (2013.01); *A61K 9/0019* (2013.01); *A61K 9/1647* (2013.01); *A61K 31/551* (2013.01); *A61K 31/5513* (2013.01); *A61K 47/34* (2013.01); *A61P 25/18* (2018.01)

(58) Field of Classification Search
CPC .... A61K 9/146; A61K 9/0019; A61K 9/1647; A61K 31/551; A61K 31/5513; A61K 47/34; A61P 25/18
USPC ....................................................... 514/220
See application file for complete search history.

(56) References Cited

U.S. PATENT DOCUMENTS

| | | | |
|---|---|---|---|
| 6,169,084 | B1 | 1/2001 | Bunnell et al. |
| 7,658,998 | B2 | 2/2010 | Brown et al. |
| 2006/0154918 | A1 | 7/2006 | Liversidge et al. |
| 2013/0177603 | A1 | 7/2013 | Gutierro et al. |
| 2014/0323517 | A1 | 10/2014 | Whelan |
| 2017/0079985 | A1 | 3/2017 | Smith et al. |
| 2018/0163911 | A1 | 6/2018 | Lutman |
| 2018/0263911 | A1 | 9/2018 | Claassen-Punt et al. |
| 2018/0264001 | A1 | 9/2018 | Smith et al. |

FOREIGN PATENT DOCUMENTS

| | | |
|---|---|---|
| CN | 103417492 A | 12/2013 |
| CN | 103877005 A | 6/2014 |
| KR | 10-2012-0048810 A | 5/2012 |
| WO | 99/12549 A3 | 5/1999 |
| WO | 01/91720 A2 | 12/2001 |
| WO | 2004/002456 A1 | 1/2004 |
| WO | 2004/052336 A2 | 6/2004 |
| WO | 2005/002625 A2 | 1/2005 |
| WO | 2005/048952 A2 | 6/2005 |
| WO | 2005/070332 A1 | 8/2005 |
| WO | 2005/087201 A1 | 9/2005 |
| WO | 2005/115599 A1 | 12/2005 |
| WO | 2005/117830 A1 | 12/2005 |
| WO | 20071011955 A2 | 1/2007 |
| WO | 2007/041410 A2 | 4/2007 |
| WO | 2007/139744 A2 | 12/2007 |
| WO | 2008/008363 A1 | 1/2008 |
| WO | 2008/104635 A1 | 9/2008 |
| WO | 2008/117927 A1 | 10/2008 |
| WO | 2008/130158 A1 | 10/2008 |
| WO | 2008/153611 A2 | 12/2008 |
| WO | 2009/068708 A2 | 6/2009 |
| WO | 2009/091737 A2 | 7/2009 |
| WO | 2009/148580 A2 | 12/2009 |
| WO | 2010/018159 A1 | 2/2010 |
| WO | 2010/040188 A1 | 4/2010 |
| WO | 2010/075072 A2 | 7/2010 |
| WO | 2010/105093 A2 | 9/2010 |
| WO | 2011/008363 A1 | 1/2011 |
| WO | 2011/042453 A1 | 4/2011 |
| WO | 2011/080733 A1 | 7/2011 |
| WO | 2011/083086 A1 | 7/2011 |
| WO | 2011/151355 A1 | 12/2011 |
| WO | 2011/151356 A2 | 12/2011 |
| WO | 2012/019009 A1 | 2/2012 |
| WO | 2012/064088 A2 | 5/2012 |
| WO | 2012/080986 A1 | 6/2012 |

(Continued)

OTHER PUBLICATIONS

Zyprexa Relprevv Label approved on Jul. 23, 2015.
Zyprexa label_2009.
Thomson Scientific Accession No. XP_002764432, "Biodegradable microsphere comprises 10-50 wt.% olanzapine or its salt, 0-5-20 wt.% release modifiers, and 30-89.5 wt.% poly(lactic-co-glycolic) acid", 2014, 4 pages.
Rovi Analysts' day, Letrozole: Key Treatment for Hormone Responsive Breast Cancer, 2010.
Pattni et al., "New Developments in Liposomal Drug Delivery", Chemical Reviews, 2015, 115(19), 10938-10966.
NDA 22-173 Pharmacology Review (Zyprexa Relprew): 2010.

(Continued)

*Primary Examiner* — Yevgeny Valenrod

(74) *Attorney, Agent, or Firm* — BakerHostetler

(57) ABSTRACT

The disclosure is directed to methods of treating schizophrenia or bipolar disorder by subcutaneously administering a sustained-release dosage form of olanzapine, or a pharmaceutically acceptable salt thereof. Methods of subcutaneously administering olanzapine, or a pharmaceutically acceptable salt thereof, are also described.

58 Claims, 2 Drawing Sheets

(56) References Cited

FOREIGN PATENT DOCUMENTS

| WO | 2012/090070 A2 | 7/2012 |
|----|----------------|--------|
| WO | 2013/036309 A2 | 3/2013 |
| WO | 2013/063125 A1 | 5/2013 |
| WO | 2013/112434 A1 | 8/2013 |
| WO | 2014/164754 A1 | 10/2014 |
| WO | 2014/202214 A1 | 12/2014 |
| WO | 2017/053346 | 3/2017 |
| WO | 2017/119928 A1 | 7/2017 |
| WO | 2017/119936 A1 | 7/2017 |

OTHER PUBLICATIONS

MH112240—For Release, Center for Scientific Review Special Emphasis Panel; Jun. 30, 2016.
McDonnell et al., "Post-injection delirium/sedation syndrome in pateints with schizophrenia treated with olanzapine long-acting injection, II: investigations of mechanism", BMC Psychiatry, 2010, 10(1), 10 pages.
Luan, H. et al., Biodegradable Microsphere Comprises Olanzapine, Releases Modifiers, and Poly(Lactic-co-glycolic) Acid:, Clarivate Analytics, 2014.
Hu, L. et al., "Current Advances in Sustained-Release Injectable Preparations", International Journal of Pharmaceutical Sciences and Research, 2012, 3(9), 2888-2896.
Hoffman, A., "Hydrogels for Biomedical Applications", Advanced Drug Delivery Reviews, 54, 2002, 3-12.
Guidance for Industry, U.S. Department of Health and Human Services Food and Drug Administration, Jul. 2005.
Frampton, J., "Olanzapine Long-Acting Injection: A Review of its Use in the Treatment of Schizophrenia", 2010 70(17) 2289-2313.
Di Lorenzo, R. et al., "Profile of Olanzapine Long-Actiong Injection for the Maintenance Treatment of Adult Patients with Schizophrenia", Neuropsychiatric Disease and Treatment, 2010, 6, 573-581.
Detke et al., "Post-injection delirium/sedation syndrome in patients with schizophrenia treated with olanzapine long-acting injection, I: analysis of cases", BMC Psychiatry, 2010, 10:43, 10 pages.
D'Souza, et al., "Preparation, Characterization, and In Vivo Evaluation of Olanzapine Poly (D,L-lactide-co-glycolide) Microspheres", Hindawi Publishing Corporation Journal of Pharmaceutics, vol. 2013, 9 pages, Jun. 2013.
D' Souza, S. et al., "IVIVC from Long Acting Olanzapine Microspheres", International Journal of Biomaterials, 2014, 23(12) 1-11.
Bushe, C. et al., "Olanzapine Long-Acting Injection: a Review of First Experiences of Post-Injection Delirium/Sedation Syndrome in Routine Clinical Practice", BMC Psychiatry, 2015, 1-8.
Bishara, D. et al., "Upcoming Agents for the Treatment of Schizophrenia", Drugs, 2008, 68 (16) 2269-2292.
Alkermes, Inc., United States Securites and Exchange Commision, Form 10-K, Annual Report Pursuant to Section 13 or 15(d) of the Securities Exchange Act of 1934, Mar. 31, 2010.
Al-Tahami et al., "Smart Polymer Based Delivery Systems for Peptides and Proteins", Recent Patents on Drug Delivery & Formulation, 2007, 1(1), 65-71.
Paquette, et al., Long-Acting Atypical Antipsychotics: Characterization of the Local Tissue Response; (2014) 2065-2077.
Database WPI Week 201421 Thomson Scientific, London, GB; An 2014-C14022 & CN 103 417 492 A Shanghai Modem Medicine Preparation Eng. Dec. 4, 2013.
McDonald David P. et al., "Post-Injection delirium/sedation syndrome in patients with schizophrenia treated with olanzapine long-acting injection, II: Investigations of Mechanism", BMC Psychiatry, Jun. 10, 2010, vol. 10, No. 1, p. 45, XP021075556.
Orange Book: Approved Drug Products with Therapeutic Equivalence Evaluations FDA (D5) 1-3, 7, 8, 13, 14 https://www.accessdata.fda.gov/scripts/cder/ob/results product.cfm?Appl Type=N&Appl No=022173 https://www.accessdata. fda.qov /druqsatfda docs/1 abel/ 2009/0221731 bl. pdf (Jun. 29, 2019).
Pierre Chue & James Chue (2012) A review of olanzapine pamoate, Expert Opinion on Pharmacotherapy, 13:11, pp. 1661-1670, DOI: 10.1517/14656566.2012.686169, Jun. 30, 2012.
Heres, et al., Pharmacokinetics of olanzapine long-acting injection: the clinical perspective. Int Clin Psychopharmacol., Nov. 2014, vol. 29, No. 6, pp. 299-312.
International Preliminary Report on Patentability and Written Opinion, International Application No. PCT/IB2018/000374, dated Jun. 25, 2018, 8 pages.
International Preliminary Report on Patentability and Written Opinion, International Application No. PCT/US2016/052757, dated Nov. 30, 2016, 7 pages.
Pervaiz, et al., Formulation and Evaluation of Parenteral Depot Drug Delivery of Atypical Antipsychotic Drug in the Treatment of Schizophrenia. PhD dissertation, Dec. 2014, 142 pages, and attached indexing document (3 pages).

SUSTAINED RELEASE OLANZAPINE FORMULATIONS

CROSS REFERENCE TO RELATED APPLICATIONS

This application claims the benefit of U.S. Provisional Application No. 62/473,608, filed Mar. 20, 2017, the entirety of which is incorporated by reference herein.

BACKGROUND OF THE DISCLOSURE

Schizophrenia is a severely debilitating psychotic disorder characterized by positive symptoms (e.g., delusions, hallucinations, and grossly disorganized or catatonic behavior) and negative symptoms (e.g., affective flattening, alogia, and avolition). Cognitive deficits are common; they include impairments of executive functioning and attention and difficulties with short- and long-term memory.

The worldwide lifetime morbidity risk of the disorder is about 1% across diverse geographic, cultural, and socioeconomic regions. Since, in most patients, the disease follows a chronic course with long-lasting impairment, long-term treatment with antipsychotic agents is usually required. Noncompliance and high discontinuation rates are particularly problematic in patients with schizophrenia. Premature discontinuation of antipsychotic drug therapy is a common phenomenon; in a recent study, 74% of patients discontinued their drug within 18 months due to either poor tolerability or lack of efficacy. Even among those who do not explicitly discontinue drug therapy, non-adherence to long-term oral medication regimens is one of the most significant therapeutic issues in the therapy of schizophrenia and related disorders. As a result, many of these patients do not experience the full benefit of antipsychotic drug therapy and suffer frequent relapses or exacerbations that require re-hospitalization, often in the context of psychiatric emergency.

Bipolar disorder is characterized by episodic disturbances in mood, energy, and activity. The definition of International Statistical Classification of Diseases and Related Health Problems 10 (ICD 10) requires two or more episodes in which the patient's mood and activity levels are significantly disturbed for diagnosis. These must include disturbances consisting on some occasions of an elevation of mood and increased energy and activity (hypomania or mania) and on others of a lowering of mood and decreased energy and activity (depression). Some patients also experience mixed episodes which include features of both mania and depression simultaneously. Repeated episodes of hypomania or mania only are classified as bipolar. The disorder is sometimes known by the terms bipolar affective disorder or manic depression. To date, there is no long acting injectable product in the U.S. approved for this indication other than Janssen's Risperdal Consta®.

Olanzapine is a well characterized and commonly prescribed atypical antipsychotic drug available in oral and parenteral formulations.

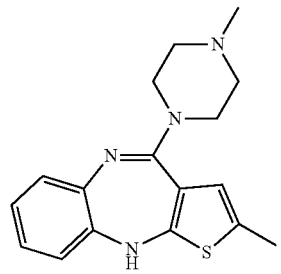

Olanzapine

Oral formulations of olanzapine and a long acting intramuscular (IM) depot preparation (ZYPREXA RELPREVV®, Eli Lilly) containing olanzapine pamoate are approved in the US for the treatment of adults and adolescents affected by schizophrenia. The oral formulations of olanzapine are also approved in the US for the treatment of bipolar I disorder. A rapid-acting IM formulation of olanzapine is approved for the treatment of adults with acute agitation associated with schizophrenia or bipolar I mania.

Although oral formulations of olanzapine and the long acting intramuscular injection preparations appear to have comparable efficacy in treating schizophrenia, administration of the long acting injection is associated with an adverse event termed "post-injection syndrome" or "post-injection delirium/sedation syndrome (PDSS)." Indeed, ZYPREXA RELPREVV's prescribing information includes a "black box" warning instructing that "Patients are at risk for severe sedation (including coma) and/or delirium after each injection and must be observed for at least 3 hours in a registered facility with ready access to emergency response services."

Thus, there exists the need for a long-acting injectable olanzapine antipsychotic agent, capable of increasing compliance in patients with schizophrenia or bipolar disorder with a prolonged delivery and which is free of the adverse effects associated with the currently approved product.

SUMMARY OF THE INVENTION

The present disclosure relates to methods of treating schizophrenia or bipolar disorder in a patient comprising subcutaneously administering to the patient, with a frequency of no more than once per 21 days, a sustained-release pharmaceutical dosage form comprising olanzapine, or a pharmaceutically acceptable salt thereof. The sustained-release pharmaceutical dosage forms of the disclosure provide a therapeutically effective dose of olanzapine for a period of at least 21 days; wherein the upper limit of a 95% Confidence Interval (CI) for the $C_{max,\ avg}$ is ≤100 ng/ml. In addition, the disclosed methods are performed without monitoring for PDSS.

The present disclosure also relates to methods of administering between about 150 mg and about 900 mg of olanzapine, or a pharmaceutically acceptable salt thereof, to a patient. These methods comprise subcutaneously administering to the patient a sustained-release olanzapine pharmaceutical dosage form at a frequency of no more than one per 21 days and provides for an upper limit of a 95% Confidence Interval for the $C_{max,\ avg}$ that is ≤100 ng/ml. According to these methods, the per-injection risk of PDSS being observed in the patient following the administration is less than 0.07% and/or the per-patient risk of PDSS being observed in the patient following the administration is less than 1.4%.

DETAILED DESCRIPTION OF THE DISCLOSURE

Figure 1:
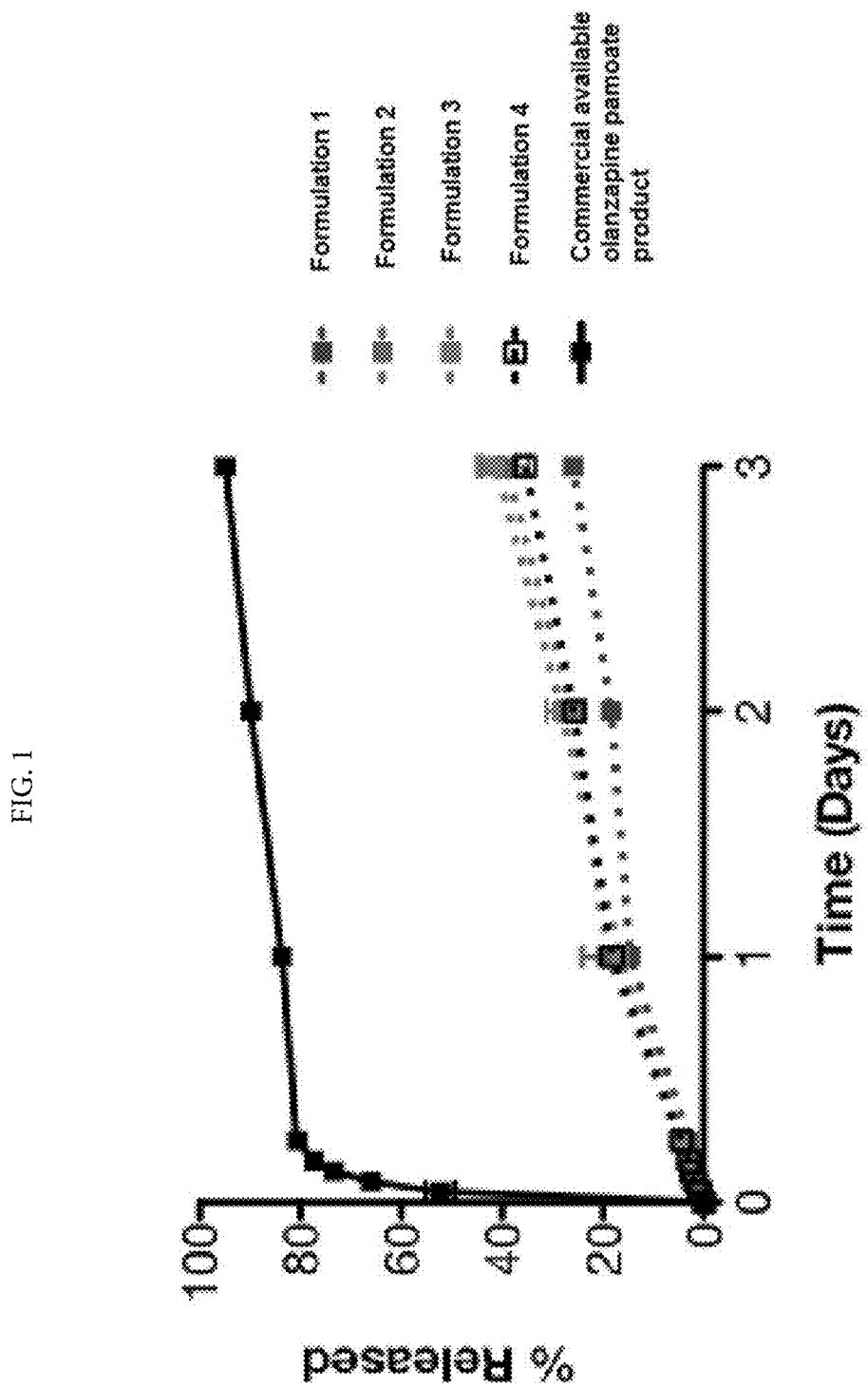
FIG. 1—is a graph that demonstrates the percentage of olanzapine released over time from different formulations.

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present disclosure is directed to methods of treating schizophrenia or bipolar disorder in a patient. These methods comprise subcutaneously administering to the patient, with a frequency of no more than once per 21 days, a sustained-release pharmaceutical dosage form comprising olanzapine, or a pharmaceutically acceptable salt of olanzapine. According to these methods, the described dosage forms provide a therapeutically effective dose of olanzapine for a period of at least 21 days. In addition, the described methods are performed without monitoring for PDSS.

The present disclosure is also directed to methods of administering between about 150 mg and about 900 mg of olanzapine, or a pharmaceutically acceptable salt thereof, to a patient. According to these methods, a sustained-release olanzapine pharmaceutical dosage form is subcutaneously administered to the patient at a frequency of no more than once per 21 days. In addition, the risk of PDSS being observed in the patient following the administration is less than 0.07% of all subcutaneous administrations, e.g., less than 0.07% of all administered injections.

The present disclosure is also directed to methods of administering a sustained-release pharmaceutical dosage form comprising olanzapine, or a pharmaceutically acceptable salt of olanzapine wherein the dosage form provides an upper limit of a 95% Confidence Interval for the $C_{max,\ avg}$ that is ≤100 ng/ml.

As used herein the term "sustained release pharmaceutical dosage form" refers to a dosage form that provides for the gradual release of olanzapine over a period of time that is preferably at least 21 days. More specifically, the release of olanzapine into the patient's bloodstream is controlled predominantly by the ingredients of the dosage form rather than by any properties of the olanzapine, or pharmaceutically acceptable salt thereof. Preferably, although not necessarily, the olanzapine release levels over the period of time are relatively constant. "Sustained release pharmaceutical dosage form," as used herein, is to the exclusion of ZYPREXA RELPREVV, wherein the release of the olanzapine into the bloodstream is controlled predominantly by the rate of dissociation of olanzapine from its pamoate salt and the subsequent absorption of the olanzapine into the bloodstream rather than by other ingredients of said composition.

The pharmaceutical dosage forms of the disclosure shall encompass dosage forms that are suitable for use with humans without undue toxic side effects. Dosage forms within the scope of the disclosure include the active pharmaceutical ingredient, or a salt form thereof, and at least one pharmaceutically acceptable carrier or excipient. Examples of pharmaceutical dosage forms of the invention include, for example, microcapsules, nanocapsules, microspheres, nanospheres, microparticles, nanoparticles, polymer-drug conjugates, micelles, liposomes, hydrogels and other in-situ forming depots or implants. Said dosage forms can be formulated using biodegradable polymers or other suitable materials using methods known in the art.

Examples of biodegradable polymers useful for preparing the dosage forms of the disclosure include poly(lactide), poly(glycolide), poly(lactide-co-glycolide), poly-1-lactic acid, poly-d-lactic acid, poly(glycolic acid), copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-captolactone), poly(amino acid), polyesteramide, polyanhydrides, polyphosphazines, poly(alkylene alkylate), biodegradable polyurethane, polyvinylpyrrolidone, polyalkanoic acid, polyethylene glycol, copolymer of polyethylene glycol and polyorthoester, albumin, chitosan, casein, waxes or blends or copolymers thereof.

Examples of platform technologies that are useful in preparing the sustained release pharmaceutical dosage forms of the present disclosure include those associated with Novartis (see, e.g., WO2010018159), Alkermes (see, e.g., WO200191720), Allergan (see, e.g., WO2013112434), Reckitt Benckiser (see, e.g., WO2009091737), Icon Bioscience (see, e.g., WO2013036309), Flamel Technologies (see, e.g., WO2012080986), QLT (see, e.g., WO2008153611), Rovi Pharmaceuticals (see, e.g., WO2011151356), Dong-A (see, e.g., WO2008130158), Durect (see, e.g., WO2004052336), NuPathe (see, e.g., WO2005070332), Ascendis Pharma (see, e.g., WO2011042453), Endo (see, e.g., WO2013063125), Delpor (see, e.g., WO2010105093), PolyActiva (see, e.g., WO2010040188), Flexion Therapeutics (see, e.g., WO2012019009), pSivida (see, e.g., WO2005002625), Camurus (see, e.g., WO2005117830), Bind Therapeutics (see, e.g., WO2010075072), Zogenix (see, e.g., WO2007041410), Ingell (WO2011083086), Foresee Pharmaceuticals (see, e.g., WO2008008363), Medincell (see, e.g., WO2012090070), Mapi Pharma (see, e.g., WO2011080733), DelSiTech (see, e.g., WO2008104635), OctoPlus (see, e.g., WO2005087201), Nanomi (see, e.g., WO2005115599), Peptron (see, e.g., WO2008117927), GP Pharm (see, e.g., WO2009068708), Pharmathen (see, e.g., WO2014202214), Titan Pharmaceuticals (see, e.g., WO2007139744), Tolmar (see, e.g., WO2009148580), Heron Therapeutics (see, e.g., US2014323517) and Intarcia Therapeutics (see, e.g., WO2005048952). The disclosures of each of these published international patent applications are incorporated herein by reference in their entireties. Methods for formulating an active ingredient, or a pharmaceutically acceptable salt thereof, into a dosage form suitable for use in the instant methods are also described in, for example, Hu et al., IJPSR, 2012; vol. 3(9): 2888-2896; Hoffman, Adv. Drug. Del. Rev. 54 (2002) 3-12; Al-Tahami et al. Recent Patents on Drug Del. & Formulation 2007, 1 65-71; Pattni et al. Chem. Rev. 2015 May 26; and Wright and Burgess (ed.) Long Acting Injections and Implants (2012), the disclosures of which are incorporated herein by reference in their entireties.

The term "monitoring for post-injection delirium/sedation syndrome" shall encompass the monitoring of a patient in a registered healthcare facility with ready access to emergency response services wherein a healthcare professional must continuously observe the patient at said healthcare facility for at least 3 hours for symptoms consistent with olanzapine-induced PDSS.

As used herein, the term "post-injection delirium/sedation syndrome" or "PDSS" shall be understood to be defined as those symptoms or combination of symptoms and circumstances as defined in Detke, H. C. et al, *BMC Psychiatry* 2010, 10:43, which is incorporated by reference herein, or as any physician skilled in the art would understand the term. For example, delirium-related symptoms include disorientation, confusion, ataxia, and dysarthria. Sedation-related symptoms include, for example, somnolence, sedation, or other change in level of consciousness.

The term 'patient' shall mean a human subject who has previously been diagnosed with schizophrenia and/or bipolar disorder. In one embodiment, the term shall apply to a human subject who is treatment naïve for each of said conditions. In another embodiment, the term shall apply to a human subject who has previously been treated for either schizophrenia or bipolar disorder but is currently not receiving pharmaceutical treatment for either. In yet another embodiment, the term shall apply to a human subject who is receiving concomitant pharmaceutical therapy for schizophrenia and/or bipolar disorder.

The olanzapine used in the methods of the disclosure can be present in the dosage forms as either olanzapine or as a pharmaceutically acceptable salt of olanzapine. Examples of pharmaceutically acceptable salts include tartrate salt, such as a (D)(−) tartrate salt or a (/−)(+) tartrate salt, a hydrochloride salt, a citrate salt, a malate salt, particularly a D-malate salt, a fumarate salt, a succinate salt, a benzoate salt, a benzenesulfonate salt, a pamoate salt, a formate salt, a malonate salt, a 1,5-naphthalenedisulfonate salt, a salicylate salt, a cyclohexanesulfamate salt, a lactate salt, a mandelate salt, particularly an (R)(−) mandelate salt, a glutarate salt, an adipate salt, a squarate salt, a vanillate salt, an oxaloacetate salt, an ascorbate salt, particularly an (L)-ascorbate salt and a sulfate salt.

As used herein, "subcutaneously administered" refers to administration into the layer of skin that is directly below the dermis and epidermis. The term specifically excludes intramuscular and intravenous methods of administration. Preferred methods of subcutaneous administration include subcutaneous injections and implants. Administration of the formulations disclosed herein is safe and efficacious and lessens the risk of PDSS associated with intramuscular (IM) injection of olanzapine, for example by unintentional blood vessel injury or intravascular injection. In some embodiments, administration of the formulations disclosed herein reduces the risk of PDSS. In some embodiments, administration of the formulations disclosed herein eliminates the risk of PDSS.

As used herein, a "therapeutically effective dose" refers to the amount of olanzapine that is sufficient to alleviate the positive and/or negative symptoms of schizophrenia and/or bipolar disorder in the patient.

As used herein, the term "95% Confidence Interval" shall mean the observed interval estimate from the sampled population containing 95% of the population mean. The term "upper limit of a 95% Confidence Interval" shall mean the highest value of said 95% Confidence Interval. The "sampled population" from which the 95% confidence interval is derived is a population of subjects undergoing a study in which pharmacokinetics is assessed for the purpose of a regulatory submission. Such studies include single ascending dose studies, multiple ascending dose studies, and safety studies, and include studies of the type required by regulatory authorities to demonstrate bioavailability and/or bioequivalence. The characteristics of subject populations used in such studies are generally set forth in various regulatory guidances, including, for example:

*Guidance for Industry: Bioavailability and Bioequivalence for Orally Administered Dug products—General Considerations* (U.S. Department of Health and Human Services, Food and Drug Administration, Center For Drug Evaluation and Research (CDER) March 2003, BP, Revision 1.)

*Guidance for Industry: Bioavailability and Bioequivalence Studies Submitted in NDAs or INDs—General Considerations Draft Guidance* (U.S. Department of Health and Human Services, Food and Drug Administration, Center For Drug Evaluation and Research (CDER) March 2014, Biopharmaceutics).

*Guideline On The Investigation Of Bioequivalence* European Medicines Agency, Committee For Medicinal Products For Human Use (CHMP), London, 20 Jan. 2010 (Doc. Ref.: CPMP/EWP/QWP/1401/98 Rev. 1/Corr**).

*Guidance for Industry: Bioequivalence Studies with Pharmacokinetic Endpoints for Drugs Submitted Under an ANDA Draft Guidance* (U.S. Department of Health and Human Services, Food and Drug Administration, Center For Drug Evaluation and Research (CDER) December 2013, Biopharmaceutics).

As used herein, the term "$C_{max, avg}$" shall mean the mean (i.e., average) observed maximum plasma level of olanzapine in subjects participating in a study in which pharmacokinetics is assessed for the purpose of a regulatory submission. Such studies include single ascending dose studies, multiple ascending dose studies, and safety studies, and include studies of the type required by regulatory authorities to demonstrate bioavailability and/or bioequivalence. The basic design and conduct of such studies is generally outlined in various regulatory guidances, including:

*Guidance for Industry: Bioavailability and Bioequivalence for Orally Administered Dug products—General Considerations* (U.S. Department of Health and Human Services, Food and Drug Administration, Center For Drug Evaluation and Research (CDER) March 2003, BP, Revision 1.)

*Guidance for Industry: Bioavailability and Bioequivalence Studies Submitted in NDAs or INDs—General Considerations* Draft Guidance (U.S. Department of Health and Human Services, Food and Drug Administration, Center For Drug Evaluation and Research (CDER) March 2014, Biopharmaceutics).

*Guideline On The Investigation Of Bioequivalence* European Medicines Agency, Committee For Medicinal Products For Human Use (CHMP), London, 20 Jan. 2010 (Doc. Ref.: CPMP/EWP/QWP/1401/98 Rev. 1/Corr**).

*Guidance for Industry: Bioequivalence Studies with Pharmacokinetic Endpoints for Drugs Submitted Under an ANDA Draft Guidance* (U.S. Department of Health and Human Services, Food and Drug Administration, Center For Drug Evaluation and Research (CDER) December 2013, Biopharmaceutics).

Each of the above guidances is incorporated herein by reference in its entirety.

The term "$C_{max,\ ind}$" shall mean the observed maximum plasma level of olanzapine in any individual subject whose drug level has been assessed within in a study in which pharmacokinetics is assessed for the purpose of a regulatory submission. Such studies include single ascending dose studies, multiple ascending dose studies, and safety studies, and include studies of the type required by regulatory authorities to demonstrate bioavailability and/or bioequivalence. As discussed above, the basic design and conduct of such studies is generally outlined in various regulatory guidances, including those mentioned above which have been incorporated by reference herein.

If subjects are included in the foregoing pharmacokinetic studies that have a non-zero baseline plasma level of olanzapine prior to administration with the subcutaneous dose of olanzapine, the baseline olanzapine plasma level shall be removed from the apparent maximum plasma concentration of olanzapine when calculating "$C_{max,\ avg}$" and "$C_{max,\ ind}$".

The dosage forms of the disclosure comprise between about 150 mg and about 900 mg of olanzapine or an amount of a pharmaceutically acceptable salt of olanzapine that is equivalent to between about 150 mg and about 900 mg of olanzapine. As used herein, reference to a specified amount or range of amounts of "olanzapine or a pharmaceutically acceptable salt thereof" shall mean that the amount of any pharmaceutically acceptable salt of olanzapine is equivalent to the specified amount or range of amounts of olanzapine.

In some embodiments, the dosage forms of the disclosure comprise between about 300 mg and about 600 mg of olanzapine or a pharmaceutically acceptable salt thereof. For example, the dosage forms of the disclosure can comprise about 150, 200, 250, 300, 350, 400, 450, 500, 550, or about 600 mg of olanzapine or a pharmaceutically acceptable salt thereof. Preferred dosage forms of the disclosure will include about 300 mg of olanzapine or a pharmaceutically acceptable salt thereof. Other preferred dosage forms of the disclosure will include about 405 mg of olanzapine or a pharmaceutically acceptable salt thereof. Yet other preferred dosage forms of the disclosure will include about 600 mg of olanzapine or a pharmaceutically acceptable salt thereof.

The dosage forms of the disclosure will provide a therapeutically effective dose of olanzapine for at least 21 days. In some embodiments, the dosage forms provide a therapeutically effective dose of olanzapine for at least about 30 days, 45 days, 60 days, or 90 days.

According to the described methods, the dosage form can be administered at a frequency of no more than once per month (i.e., no more than once in about 30 days). Alternatively, the dosage form can be administered at a frequency of no more than once about every two months (i.e., no more than once in about 60 days). In other methods, the dosage form can be administered at a frequency of once per three months (i.e., no more than once in about 90 days).

A person of ordinary skill in the art would understand references to numbers of days herein to refer to periods of time such that, for example, the expression "for at least about 30 days" would be understood as equivalent to "for a period of at least about 30 days"; the expression "for at least about 60 days" would be understood as equivalent to "for a period of at least about 60 days"; the expression "for about 90 days" would be understood as equivalent to "for a period of about 90 days."

In preferred embodiments, the dosage forms of the invention can be administered as a therapeutically effective medication without the need for an initial titration period of higher, or more frequent, "starter" dosages and/or without the need for additional coverage by an oral olanzapine product during this initial stage of therapy.

The methods of the disclosure result in a per-patient risk of olanzapine-induced PDSS being less than that observed with ZYPREXA RELPREVV. As used herein, the term "per-patient risk of olanzapine-induced PDSS" means the risk of developing olanzapine-induced PDSS that a patient undergoing treatment in accordance with the methods of the present invention is likely to face, regardless of the number of treatments. For example, using the methods and/or dosage forms of the disclosure, results in a per-patient risk of olanzapine-induced PDSS of less than 1.4%. In preferred embodiments, the risk of olanzapine-induced PDSS occurring on a per-patient basis, using the methods and/or dosage forms of the disclosure, is less than 1%, less than 0.75%, less than 0.5%, less than 0.25%, less than 0.1%, or less than 0.05%. In some embodiments, the per-patient risk of olanzapine-induced PDSS occurring in the patient using the methods and/or dosage forms of the present disclosure is so small as to be undeterminable, i.e., essentially a 0% risk. Statistical methods of determining the risk of olanzapine-induced PDSS occurring on a per-patient basis are known in the art.

The methods of the disclosure result in a per-administration, e.g., per-injection, risk of olanzapine-induced PDSS of less than that observed following administration of ZYPREXA RELPREVV. As used herein, the term "per-injection risk of olanzapine-induced PDSS" means the risk of developing olanzapine-induced PDSS that a patient undergoing treatment in accordance with the methods of the present invention is likely to face from a single injection. Using the methods and/or dosage forms of the disclosure, results in a per-injection risk of olanzapine-induced PDSS of less than 0.07% of all subcutaneous administrations, e.g., less than 0.07% of all administered injections. In preferred embodiments, the per-injection risk of olanzapine-induced PDSS occurring in a patient, using the methods and/or dosage forms of the disclosure, is less than 0.01%, less than 0.005%, less than 0.001%, or less than 0.0005%. In some embodiments, the per-injection risk of olanzapine-induced PDSS occurring in the patient using the methods and/or dosage forms of the disclosure is so small as to be undeterminable, i.e., essentially a 0% risk to the patient. Statistical methods of determining the per-injection risk of olanzapine-induced PDSS occurring in the patient are known in the art.

Prior reports have indicated that the dissolution rate of olanzapine pamoate is significantly higher in plasma than it is in aqueous solutions, such as a phosphate buffer (for example, see McDonnell et al., "Post-injection delirium/sedation syndrome in patients with schizophrenia treated with olanzapine long-acting injection, II: investigations of mechanism" *BMC Psychiatry* (2010); v. 10: 45, incorporated herein by reference in its entirety). It has been hypothesized that this increased dissolution rate for the pamoate salt may be relevant to the mechanisms that underlie occurrences of PDSS that have occurred following IM administration of ZYPREXA RELPREVV (id.). Episodes of PDSS have been correlated with plasma olanzapine concentrations of from about 100 ng/ml to nearly 700 ng/ml following administration (id.). It has been speculated that PDSS might occur when a portion of an intramuscularly-injected olanzapine pamoate dose accidentally enters the bloodstream as a result of injury to a blood vessel during the injection process (id.). It is unclear how such accidental bloodstream entry during intramuscular administration can be predictably avoided (id.).

In the subcutaneously-administered dosage forms of the disclosure, however, the release of olanzapine into the patient's bloodstream is controlled so as to predictably avoid rapid increases in olanzapine plasma concentration. This control is predominantly achieved by the ingredients of the dosage form rather than by any properties of a particular olanzapine salt. As such, the disclosed dosage forms avoid the risk of an accelerated plasma dissolution rate, providing for a decreased risk of a patient experiencing PDSS.

The sustained-release profiles of the dosage forms of the disclosure are achieved by the gradual release of olanzapine, or a pharmaceutically acceptable salt for thereof, from the dosage form into the patient's bloodstream over a period of time that is at least about 21 days. Preferably, the gradual release of olanzapine, or a pharmaceutically acceptable salt thereof from the dosage form into the patient's bloodstream provides for an upper limit of a 95% Confidence Interval for the $C_{max,\ avg}$ that is ≤100 ng/ml, ≤90 ng/ml, ≤80 ng/ml, ≤70 ng/ml, ≤60 ng/ml, or ≤50 ng/ml. In a preferred embodiment, the gradual release of olanzapine, or a pharmaceutically acceptable salt thereof from the dosage form into the patient's bloodstream provides for a $C_{max,\ ind}$ of ≤100 ng/ml, of ≤90 ng/ml, ≤80 ng/ml or of ≤70 ng/ml. Methods of determining the amount of olanzapine released into human plasma are known in the art.

In preferred embodiments, the methods of the disclosure do not produce a plasma concentration of olanzapine, or a pharmaceutically acceptable salt form thereof, of greater than 50 ng/ml at any point within 60 hours of administration. In further embodiments the methods of the disclosure do not produce a plasma concentration of olanzapine, or a pharmaceutically acceptable salt form thereof, of greater than 25 ng/ml at any point within 60 hours of administration.

The following examples serve to illustrate the present invention without limiting it:

EXAMPLES

Example 1

Formulations of the disclosure can be prepared according to methods known in the art. For example, formulations of the disclosure can be produced by the following steps:

Step 1: Preparation of Feed Solutions for Microparticle Formation Step and Downstream Processing.

For the preparation of 1 liter surfactant solution, the calculated amount of surfactant is weighed by means of a precision balance into a vessel containing a magnetic stir bar. Afterwards, ultrapure water is added so that the resulting volume is slightly below 1 liter. The surfactant is dissolved under agitation with the magnetic stir bar at an appropriate temperature. Finally, ultrapure water is added so that a volume of exactly 1 liter is achieved.

Olanzapine is weighed by means of an analytical balance into a second vial containing a magnetic stir bar. The respective volume of solvent is added by means of a glass pipette. The actual mass of the solvent is determined by differential weighing.

The polymer is weighed by means of a precision balance into a third glass vessel containing a magnetic stir bar. The respective volume of organic solvent is added by means of a glass pipette. The actual mass of organic solvent added to the polymer is determined by differential weighing. The polymer is dissolved at room temperature under agitation by means of the magnetic stir bar.

Step 2: Formation of Microparticles

Afore prepared polymer solution and API solution (or powder) are successively weighed into a custom-made manufacturing vessel and are dispersed by means of a mechanical agitator. After a certain time a surfactant solution is transferred at a defined rate. This action induces a phase inversion, which in turn leads to the formation of API-loaded micro particles.

The characteristic properties of resulting micro particle formulations are either controlled by adjusting the processing conditions—e.g. the dispersing parameters (time, speed), geometric parameters (dissolver disc diameter, manufacturing vessel diameter) or the surfactant solution transfer rate, but also by the intrinsic physicochemical properties of respective feed solutions, e.g. the composition, viscosity, solubility into one another or the interfacial tension. Both categories, the processing and the physicochemical parameters, undergo an iterative optimization process in order to achieve the targeted performance of the formulation.

Resulting API-loaded micro particle suspensions will still contain excess organic solvent(s) as well as non-encapsulated API and excipients, which are each removed during the downstream processing.

Step 3: Removal of Organic Solvent(s) from the Polymeric Micro Particles by Means of Extraction Subsequent to the micro particle formation step, the suspension is transferred into a glass beaker containing a magnetic stir bar. This dilute micro particle suspension is vigorously agitated by means of magnetic stirring to facilitate the organic solvent passage from the micro particles into the extraction medium. Later, ethanol is added to the surfactant solution.

Step 4: Separation of Micro Particles

Following the extraction step, the micro particles are separated from the continuous phase by filtration. For this purpose, a pressure filtration unit is used.

In case that no filtration can be applied, the micro particles are collected from the suspension by centrifugation and the pellet containing the micro particles is resuspended with ultrapure water and centrifuged again. If required, this washing step can be repeated.

Step 5: Transfer to the Solid State

The filter cake is resuspended with a certain volume of ultrapure water to adjust the desired particle concentration, suspended, frozen and stored until freeze-drying.

The olanzapine content of the freeze-dried micro particle formulations is determined by means of HPLC.

Materials:

Olanzapine can be purchased commercially or prepared according to methods known in the art.

Resomer "RG" polymers can be purchased from Boehringer Ingelheim.

Other materials were purchased from commercial sources.

Table 1 is representative of formulations of the disclosure. "CL" refers to core loading. "ThCL" refers to the theoretical core loading. "EE" refers to encapsulation efficiency. "Morph" refers to the morphology of the olanzapine. In some examples in Table 1, a solution of 1000 mL water, 2% polyvinyl alcohol (PVA) is referred to as wash phase or "WP".

TABLE 1

| Ex. | Polymer Phase | Drug Phase | Surfactant Phase phase inversion | Surfactant Phase solvent extraction | Dispersing Vessel | Th. CL (% w/w) | CL (% w/w) | EE (5) | Morp. |
|---|---|---|---|---|---|---|---|---|---|
| 1 | 3 g RG753S in 10 mL EtFo (ethyl formate) | 2000 mg olanzapine in 8.6 mL BnOH (benzyl alcohol) | 50 mL water 1% PVA (polyvinyl alcohol) | 1000 mL water, 2% PVA after 60 min: 300 mL water, 2% PVA after 90, 120, 150 min: 100 mL water, 2% PVA 100 mL ethanol after 180 min: filtration and resuspension in 1000 mL water, 4% F68 after 240 min: filtration | 3000 rpm 21 min 2500 rpm 0.5 min D: 46 mm | 38.8 | 32.6 | 84.0 | no crystals |
| 2 | 3 g RG753S in 10 mL EtFo | 2000 mg olanzapine in 8.6 mL BnOH | 50 mL water 1% PVA | As in Ex. 1 | 3000 rpm 21 min 2500 rpm 0.5 min D: 46 mm | 38.9 | 33.9 | 87.1 | no crystals |
| 3 | 3 g RG753H in 10 mL EtFo | 2000 mg olanzapine in 8.6 mL BnOH | 50 mL water 1% PVA | As in Ex. 1 | 3000 rpm 22 min 2500 rpm 0.5 min D: 46 mm | 39.2 | 33.6 | 85.7 | no crystals |
| 4 | 3 g RG753H in 10 mL EtFo | 1500 mg olanzapine as solid | 80 mL water 8% PVA | 1000 mL water, 2% PVA after 60, 75, 90 and 105 min: addition of 50 mL ethanol after 120 min: filtration and resuspension in 500 mL water, 4% F68 | 2500 rpm 7 min 3000 rpm 13 min D: 34 mm | 33.1 | 25.5 | 77.1 | no crystals |
| 5 | 3 g RG753H in 10 mL EtFo | 1500 mg olanzapine as solid | 80 mL water 8% PVA | As in Ex. 4 | As in Ex. 4 | 33.1 | 25.5 | 77.1 | no crystals |
| 6 | 3 g RG753H in 10 mL EtFo | 1500 mg olanzapine as solid | 80 mL water 8% PVA | As in Ex. 4 | As in Ex. 4 | 33.3 | 24.1 | 72.3 | no crystals |
| 7 | 3 G RG756 in 14 mL EtFo | 2000 mg olanzapine in 8.6 mL BnOH | 50 mL water 1% PVA | As in Ex. 1 | 3000 rpm 7 min 2500 rpm 0.5 min D: 46 mm | 39.9 | 32.5 | 81.5 | no crystals |
| 8 | 3 g RG753H in 10 mL EtFo | 2000 mg olanzapine in 8.6 mL BnOH | 50 mL water 1% PVA | As in Ex. 1 | 3000 rpm 22 min 2500 rpm 0.5 min D: 46 mm | 39.2 | 34.2 | 87.1 | no crystals |
| 9 | 1.5 g RG756S in 7 mL EtFo + 1.5 g RG504 in 5 mL EtFo | 2000 mg olanzapine as solid | 80 mL water 4% PVA | As in Ex. 1 | 3000 rpm 16 min D: 34 mm | 39.9 | 30.4 | 76.2 | no crystals |
| 10 | 3 g RG753S in 10 mL EtFo | 2000 mg olanzapine in 8.6 mL BnOH | 50 mL water 1% PVA | As in Ex. 1 | 3000 rpm 21 min 2500 rpm 0.5 min D: 46 mm | 38.9 | 33.9 | 87.1 | no crystals |
| 11 | 3 g RG753H in 10 mL EtFo | 2000 mg olanzapine as solid | 80 mL water 4% PVA | 1000 mL water, 2% PVA after 60, 75, 90, 105 min: 50 mL ethanol after 120 min: filtration and resuspension in 500 mL water, 4% F68 after 150 min: filtration | 3000 rpm 40 min D: 34 mm | 39.2 | 37.6 | 95.9 | no crystals |
| 12 | 3 g RG756 in 14 mL EtFo | 2000 mg olanzapine in 8.6 mL BnOH | 50 mL water 1% PVA | As in Ex. 1 | 3000 rpm 7 min 2500 rpm 0.5 min D: 46 mm | 39.9 | 25.5 | 81.5 | no crystals |

TABLE 1-continued

| Ex. | Polymer Phase | Drug Phase | Surfactant Phase phase inversion | Surfactant Phase solvent extraction | Dispersing Vessel | Th. CL (% w/w) | CL (% w/w) | EE (5) | Morp. |
|---|---|---|---|---|---|---|---|---|---|
| 13 | 3 g RG753S in 10 mL EtFo | 2000 mg olanzapine in 8.6 mL BnOH | 50 mL water 1% PVA | 1000 mL water, 2% PVA after 60 min: 300 mL water, 2% PVA after 90, 120 and 150 min: 100 mL water, 2% PVA 100 mL ethanol after 180 min: filtration and resuspension in 1000 mL water, 4% F68 | 3000 rpm 18 min 3500 rpm 4 min 4000 rpm 4 min 2500 rpm 0.5 min D: 46 mm | 39.5 | 33.9 | 85.8 | no crystals |
| 14 | 3 g RG755S in 10 mL EtFo | 2000 mg olanzapine in 8.6 mL BnOH | 50 mL water 1% PVA | As in Ex. 1 | 3000 rpm 14.5 min 2500 rpm 0.5 min D: 46 mm | 39.7 | 31.8 | 80.0 | no crystals |
| 15 | 1.5 g RG755S + 1.5 g RG735S in 10 mL EtFo | 2000 mg olanzapine in 8.6 mL BnOH | 50 mL water 1% PVA | As in Ex. 1 | 3000 rpm 18 min 2500 rpm 0.5 min D: 34 mm | 39.3 | 33.7 | 85.7 | no crystals |
| 16 | 2.25 g RG755S + 0.75 g RG735S in 10 mL EtFo | 2000 mg olanzapine in 8.6 mL BnOH | 50 mL water 1% PVA | As in Ex. 1 | 3000 rpm 18 min 2500 rpm 0.5 min D: 34 mm | 39.3 | 32.9 | 83.6 | no crystals |
| 17 | 1.5 g RG755S + 1.5 g RG753H in 10 mL EtFO | 2000 mg olanzapine in 8.6 mL BnOH | 50 mL water 1% PVA | As in Ex. 1 | 3000 rpm 23.5 min 2500 rpm 0.5 min D: 46 mm | 39.4 | 32.7 | 82.9 | no crystals |
| 18 | 2.25 g RG755S + 0.75 g RG753H in 10 mL EtFO | 2000 mg olanzapine in 8.6 mL BnOH | 50 mL water 1% PVA | As in Ex. 1 | 3000 rpm 18 min 2500 rpm 0.5 min D: 46 mm | 39.8 | 33.2 | 83.4 | no crystals |
| 19 | 1.5 g RG755S + 1.5 g RG504H in 10 mL EtFo | 2000 mg olanzapine in 8.6 mL BnOH | 50 mL water 1% PVA | As in Ex. 1 | 3000 rpm 32 min 2500 rpm 0.5 min D: 46 mm | 39.5 | 33.0 | 83.6 | no crystals |
| 20 | 2 g RG755S + 1 g RG504H in 10 mL | 2000 mg olanzapine in 8.6 mL BnOH | 50 mL water 1% PVA | As in Ex. 1 | 3000 rpm 29.5 min 2500 rpm 0.5 min D: 46 mm | 39.9 | 21.4 | 53.7 | no crystals |
| 21 | 1.5 g RG756S in 7 mL EtFo + 1.5 g RG504 in 5 mL EtFo | 2000 mg olanzapine as solid | 80 mL water 4% PVA | 1000 mL water 2% PVA ("WP") after 60 min: 300 mL WP after 90, 120 and 150 min: addition of 100 mL WP 100 mL ethanol after 180 min: filtration and resuspension in 1000 mL water 4% F68 for 60 min filtration | 3000 rpm 18 min D: 34 mm | 40.8 | 36.1 | 88.5 | no crystals |
| 22 | 1.5 g RG757S in 8 mL EtFo + 1.5 g RG504 in 5 mL EtFo | 2000 mg olanzapine as solid | 80 mL water 4% PVA | 1000 mL water, 2% PVA ("WP") after 60 min: 300 mL WP after 90, 120 and 150 min: addition of 100 mL WP 100 mL ethanol after 180 min: filtration and resuspension in 1000 mL 100 mM citrate buffer pH 6.0, 4% F68 for 60 min Filtration | 3000 rpm 15 min D: 34 mm | 40.0 | 23.8 | 59.4 | no crystals |

TABLE 1-continued

| Ex. | Polymer Phase | Drug Phase | Surfactant Phase phase inversion | solvent extraction | Dispersing Vessel | Th. CL (% w/w) | CL (% w/w) | EE (5) | Morp. |
|---|---|---|---|---|---|---|---|---|---|
| 23 | 1.5 g RG755S in 8 mL EtFo + 1.5 g RG504 in 5 mL EtFo | 2000 mg olanzapine as solid | 80 mL water 4% PVA | As in Ex. 22 | 3000 rpm 22 min D: 34 mm | 38.9 | 30.2 | 77.5 | no crystals |
| 24 | 3 g RG753H in 12 mL EtFo (pre-dispersed) | 2000 mg olanzapine as solid | 80 mL water 4% PVA | 1000 mL water, 2% PVA ("WP") after 60, 75, 90, 105 min: 50 mL ethanol after 120 min: filtration and resuspension in 500 mL water 4% F68 for 35 min Filtration | 3000 rpm 40 min D: 34 mm | 39.3 | 36.3 | 92.3 | no crystals |
| 25 | 2.4 g RG753H in 8 mL EtFo (pre-dispersed) + 0.6 g RG504H in 4 mL EtFo | 2000 mg olanzapine as solid | 80 mL water 4% PVA | 1000 mL water, 2% PVA ("WP") after 60, 75, 90, 105 min: 50 mL ethanol after 120 min: filtration and resuspension in 1000 mL 100 mM citrate pH 6.0, 4% F68 for 35 min Filtration | 2000 rpm 10 min 3000 rpm 27 min D: 34 mm | 38.8 | 36.3 | 93.6 | no crystals |
| 26 | 2.1 g RG753H in 7 mL EtFo (pre-dispersed) + 0.9 g RG504H in 5 mL EtFo | 2000 mg olanzapine as solid | 80 mL water 4% PVA | As in Ex. 25 | 2000 rpm 20 min 3000 rpm 24.5 min D: 34 mm | 38.8 | 34.4 | 88.6 | no crystals |
| 27 | 1.5 g RG753H in 7 mL EtFo (pre-dispersed) + 1.5 g RG504H in 5 mL EtFo | 2000 mg olanzapine as solid | 80 mL water 4% PVA | 1000 mL water, 2% PVA ("WP") after 60, 75, 90, 105 min: 50 mL ethanol after 120 min: filtration and resuspension in 1000 mL water 4% F68 for 30 min. Filtration | 2000 rpm 10 min 3000 rpm 24.5 min D: 34 mm | 38.9 | 36.0 | 92.6 | no crystals |
| 28 | 1.2 g RG753H in 6 mL EtFo (pre-dispersed) + 1.8 g RG504 in 6 mL EtFo | 2000 mg olanzapine as solid | 80 mL water 4% PVA | As in Ex. 27 | 2000 rpm 10 min 3000 rpm 23 min D: 34 mm | 39.0 | 36.4 | 93.4 | no crystals |
| 29 | 0.9 g RG753H in 5 mL EtFo (pre-dispersed) + 2.1 g RG504 in 7 mL EtFo | 2000 mg olanzapine as solid | 80 mL water 4% PVA | 1000 mL water 2% PVA ("WP") after 60, 75, 90, 105 min: 50 mL ethanol after 120 min: filtration and resuspension in 1000 mL 100 mM citrate pH 6.0, 4% F68 for 30 min Filtration | 2000 rpm 10 min 3000 rpm 23 min D: 34 mm | 38.9 | 27.8 | 71.5 | no crystals |
| 30 | 3.0 g RG753H in 12 mL EtFo (pre-dispersed) | 2000 mg olanzapine as solid | 80 mL water 4% PVA | 1000 mL water, 2% PVA ("WP") after 60, 75, 90, 105 min: 50 mL ethanol after 120 min: filtration and resuspension in 500 mL water 4% F68 for 35 min Filtration | 3000 rpm 40 min D: 34 mm | 39.3 | 36.3 | 92.3 | no crystals |
| 31 | 3.0 g RG753H in 12 mL EtFo (pre-dispersed) | 2000 mg olanzapine as solid | 80 mL water 4% PVA 5% sucrose | 1000 mL water, 2% PVA ("WP") after 60, 75, 90, 105 min: 50 mL ethanol after 120 min: filtration and resuspension in 1000 mL citrate pH 6.2 4% F68 for 35 min Filtration | 3000 rpm 37 min D: 34 mm | 39.0 | 33.5 | 85.9 | no crystals |
| 32 | 3.0 g RG753H in 12 mL EtFo (pre-dispersed) | 2000 mg olanzapine as solid | 80 mL water 4% PVA 2% PEG 20k | As in Ex. 31 | 3000 rpm 35 min D: 34 mm | 39.2 | 35.8 | 91.3 | no crystals |

TABLE 1-continued

| Ex. | Polymer Phase | Drug Phase | Surfactant Phase phase inversion | Surfactant Phase solvent extraction | Dispersing Vessel | Th. CL (% w/w) | CL (% w/w) | EE (5) | Morp. |
|---|---|---|---|---|---|---|---|---|---|
| 33 | 3 g RG753H in 10 mL EtFo | 2000 mg olanzapine in 8.6 mL BnOH | 50 mL water 1% PVA | 1000 mL water, 2% PVA (wash phase "WP") after 60 min: 300 mL WP after 90, 120 and 150 min: 100 mL WP 100 mL ethanol after 180 min: filtration and resuspension in 1000 mL water, 4% F68 after 240 min: filtration | 3000 rpm 22 min 2500 rpm 0.5 min D: 46 mm | 39.2 | 34.2 | 87.1 | no crystals |
| 34 | 3 g RG753H in 10 mL EtFo | 2000 mg olanzapine in 8.6 mL BnOH | 50 mL water 1% PVA | 1000 mL water, 2% PVA ("WP") after 60 min: 300 mL WP after 90, 120 and 150 min: 100 mL WP 100 mL ethanol after 180, 210 min: 100 mL ethanol after 240 min: filtration and resuspension in 1000 mL water, 4% F68; 50 mL ethanol after 255, 270, 285 min: addition of 50 mL ethanol after 300 min: filtration | 3000 rpm 22 min 2500 rpm 0.5 min D: 46 mm | 39.0 | 35.0 | 89.9 | no crystals |
| 35 | 3 g RG755S in 10 mL EtFo | 2000 mg olanzapine in 8.6 mL BnOH | 50 mL water 1% PVA | 1000 mL water, 2% PVA ("WP") after 60 min: 300 mL WP after 90, 120 and 150 min: 100 mL WP 100 mL ethanol after 180 min: filtration and resuspension in 1000 mL water, 4% F68 after 240 min: filtration | 3000 rpm 14.5 min 2500 rpm 0.5 min D: 46 mm | 39.7 | 31.8 | 80.0 | no crystals |
| 36 | 3 g RG755S in 10 mL EtFo | 2000 mg olanzapine in 8.6 mL BnOH | 50 mL water 1% PVA | 1000 mL water, 2% PVA ("WP") after 10 min: filtration and resuspension in 1000 mL WP after 60 min: 300 mL WP after 90, 120 and 150 min: 100 mL WP 100 mL ethanol after 180, 210 min: 100 mL ethanol after 240 min: filtration and resuspension in 1000 mL water, 4% F68 50 mL ethanol after 255, 270, 285 min: addition of 50 mL ethanol after 300 min: filtration | 3000 rpm 14.5 min 2500 rpm 0.5 min D: 46 mm | 39.6 | 33.5 | 84.7 | no crystals |
| 37 | 3 g RG755S in 10 mL EtFo | 2000 mg olanzapine in 8.6 mL BnOH | 50 mL water 2% PVA | As in Ex. 36 | 3000 rpm 14.5 min 2000 rpm 0.5 min D: 46 mm | 39.7 | 33.3 | 83.9 | no crystals |
| 38 | 1.5 g RG755S + 1.5 g RG753S in 10 mL EtFo | 2000 mg olanzapine in 8.6 mL BnOH | 50 mL water 1% VPA | As in Ex. 1 | 3000 rpm 18 min 2500 rpm 0.5 min D: 34 mm | 39.3 | 33.7 | 85.7 | no crystals |
| 39 | 1.5 g RG755S + 1.5 g RG753S in 10 mL EtFo | 2000 mg olanzapine in 8.6 mL BnOH | 50 mL water 2% PVA | As in Ex. 36 | 3000 rpm 18 min 2500 rpm 0.5 min D: 34 mm | 39.4 | 32.5 | 82.6 | no crystals |

TABLE 1-continued

| Ex. | Polymer Phase | Drug Phase | Surfactant Phase phase inversion | Surfactant Phase solvent extraction | Dispersing Vessel | Th. CL (% w/w) | CL (% w/w) | EE (5) | Morp. |
|---|---|---|---|---|---|---|---|---|---|
| 40 | 1.5 g RG755S + 1.5 g RG753S in 10 mL EtFo | 2000 mg olanzapine in 8.6 mL BnOH | 50 mL water 2% PVA | As in Ex. 36 | 3000 rpm 18 min 2000 rpm 0.5 min D: 34 mm | 39.4 | 34.2 | 86.8 | no crystals |
| 41 | 3 g RG503H in 12 mL EtFo | 2000 mg olanzapine as solid | 80 mL water 4% PVA | 1000 mL water, 2% PVA ("WP") after 60 min: 300 mL WP after 90, 120 and 150 min: 100 mL WP 100 mL ethanol after 180 min: filtration and resuspension in 1000 mL citrate buffer 100 mM, pH 6.2 4% F68 for 30 min Filtration | 3000 rpm 30 min D: 34 mm | 39.0 | 36.8 | 94.5 | no crystals |
| 42 | 3 g RG504H in 12 mL EtFo | 2000 mg olanzapine as solid | 80 mL water 4% PVA | 1000 mL water, 2% PVA ("WP") after 60 min: 300 mL WP after 90, 120 and 150 min: 100 mL WP 100 mL ethanol after 180 min: filtration and resuspension in 1000 mL citrate buffer 100 mM, pH 6.2 4% F68 for 35 min Filtration | 3000 rpm 24 min D: 34 mm | 39.3 | 33.6 | 85.4 | no crystals |
| 43 | 0.6 g RG755S in 4 mL EtFo + 2.4 g RG753H in 8 mL EtFo | 2000 mg olanzapine as solid | 80 mL water 4% PVA | 1000 mL water, 2% PVA ("WP") after 60, 75, 90, 105 min: 50 mL ethanol after 120 min: filtration and resuspension in 1000 mL citrate buffer 100 mM pH 6.0, 4% F68 for 30 min Filtration | 2000 rpm 14 min 3000 rpm 25 min D: 34 mm | 39.7 | 36.3 | 91.5 | no crystals |
| 44 | 2.1 g RG753S in 7 mL EtFo + 0.9 g RG504H in 5 mL EtFo | 2000 mg olanzapine as solid | 80 mL water 4% PVA | 1000 mL water, 2% PVA ("WP") after 60, 75, 90, 105 min: 50 mL ethanol after 120 min: filtration and resuspension in 1000 mL citrate buffer 100 mM pH 6.2, 4% F68 for 40 min Filtration | 2000 rpm 22 min 3000 rpm 22 min D: 34 mm | 38.9 | 36.3 | 93.4 | no crystals |
| 45 | 2.4 g RG753H in 8 mL EtFo + 0.6 g RG504H in 4 mL EtFo | 2000 mg olanzapine as solid | 80 mL water 4% PVA | 1000 mL water, 2% PVA ("WP") after 60, 75, 90, 105 min: 50 mL ethanol after 120 min: filtration and resuspension in 1000 mL citrate buffer 100 mM pH 6.2, 4% F68 for 45 min Filtration | 2000 rpm 10 min 3000 rpm 27 min D: 34 mm | 39.4 | 30.9 | 78.5 | no crystals |
| 46 | 3.0 g RG753H in 12 mL EtFo | 2000 mg olanzapine as solid | 80 mL water 4% PVA | 2000 mL water, 2% PVA ("WP") after 30, 60, and 90 min: 100 mL ethanol after 120 min: filtration and resuspension in 1000 mL citrate buffer 100 mM, pH 6.5 4% F68 for 30 min Filtration | 2000 rpm 15 min 3000 rpm 26 min D: 34 mm | 39.0 | 38.5 | 98.7 | no crystals |
| 47 | 2.7 g RG753H in 9 mL EtFo + 0.3 g RG504H in 3 mL EtFo | 2000 mg olanzapine as solid | 80 mL water 4% PVA | As in Ex. 46 | 2000 rpm 15 min 3000 rpm 25 min D: 34 mm | 38.7 | 36.9 | 95.5 | no crystals |

TABLE 1-continued

| Ex. | Polymer Phase | Drug Phase | Surfactant Phase phase inversion | solvent extraction | Dispersing Vessel | Th. CL (% w/w) | CL (% w/w) | EE (5) | Morp. |
|---|---|---|---|---|---|---|---|---|---|
| 48 | 2.7 g RG753H in 9 mL EtFo + (0.15 g RG504H + 0.15 g RG752H in 3 mL EtFo) | 2000 mg olanzapine as solid | 80 mL water 4% PVA | As in Ex. 46 | 2000 rpm 15 min 3000 rpm 25 min D: 34 mm | 39.1 | 38.6 | 98.7 | no crystals |
| 49 | 2.7 g RG753H in 9 mL EtFo + (0.15 g RG504H + 0.15 g RG756S in 3 mL EtFo) | 2000 mg olanzapine as solid | 80 mL water in 4% PVA | As in Ex. 46 | 2000 rpm 15 min 3000 rpm 25 min D: 34 mm | 39.1 | 37.8 | 96.7 | no crystals |

Example 2

Solubility of Olanzapine Base and Olanzapine Pamoate Monohydrate Salt

The saturated solubility of olanzapine and olanzapine pamoate monohydrate were determined at both room temperature (~24-25° C.) and at physiological temperature (+37° C.) by adding an excess of the API to canine and human plasma and continuously agitating for 24 hours. In an attempt to reduce oxidation of olanzapine and olanzapine pamoate monohydrate, a water-soluble antioxidant, tocophersolan was added to the plasma. Samples were protected from light under constant agitation using a vortex mixer. The stability of the API under these conditions was assessed at timed intervals (T=0, 2, 4, 21, 24 hours and 2 and 3 days). At each time point olanzapine recovery was assessed by UPLC. See Table 2.

TABLE 2

| Medium | olanzapine Concentration (μg/ml) | SD | olanzapine pamoate monohydrate Concentration (μg/ml) | SD |
|---|---|---|---|---|
| Canine plasma, RT | 473.00 | 3.67 | | |
| Canine plasma + 1% Tocophersolan, RT | 743.69 | 176.56 | 860.96 | 35.85 |
| Canine plasma, 37° C. | 474.94 | 5.51 | | |
| Canine plasma + 1% Tocophersolan, 37° C. | 684.50 | 201.13 | 817.47 | 4.84 |
| Human plasma, RT | 586.00 | 4.55 | | |
| Human plasma + 1% Tocophersolan, RT | 935.64 | 267.45 | 697.01 | 23.95 |
| Human plasma, 37° C. | 601.95 | 7.57 | | |
| Human plasma + 1% Tocophersolan, 37° C. | 643.27 | 88.03 | 674.09 | 47.55 |

Example 3

Measuring of In Vitro Human Plasma Release Profiles of Dosage Forms

Dissolution of e.g., a 30 mg olanzapine dosage form is carried out in 50 ml of human plasma+1% tocophersolan under agitation and the rate of dissolution at +37° C. is monitored over the course of 3 days at T=1, 2, 3, 4, 6, 24, 48 and 72 hours. The experiment is carried out in triplicate and run in parallel with IVR of formulations.

3×50 ml aliquots of plasma+1% tocophersolan are pipetted into 3×50 ml low protein binding tubes. Using a syringe and a 19G needle, 200 μl of the reconstituted olanzapine dosage form is taken up into the syringe, equating to a 30 mg dose. In order to accurately calculate the true mass and volume injected, the syringe is weighed without the cap and the mass is recorded. Subsequently, the syringe containing the 30 mg dose of olanzapine is plunged centrally into the plasma media and the content is slowly ejected. The empty syringe is weighed once more (without the cap) and the mass injected is recorded. Once all samples are prepared they are incubated at +37° C. in a temperature controlled shaking incubator (180 rpm).

At the time of sampling the 3×50 ml tubes are immediately centrifuged at 2000 rpm for 10 minutes at +20° C. using a Jouan CR3i centrifuge (France). This allows separation of the olanzapine dosage form precipitate from the plasma. After centrifugation an aliquot of 1 ml is taken from each 50 ml tube and is pipetted into a 2 ml low protein binding tube and is stored as a backup at −20° C. An additional 0.5 ml of supernatant is taken from each sample and is pipetted into a separate 2 ml low protein binding tube.

Protein precipitation is carried out on each sample as follows. Plasma samples are mixed with acetonitrile using a 1:2 ratio (sample:acetonitrile), are vortexed thoroughly for approximately 5 minutes, are allowed to stand for 5 minutes (allowing protein precipitation) before being centrifuged for 10 minutes at 16,000 g at +20° C. using a Eppendorf 5415R centrifuge (USA). Subsequently the supernatant is removed and is diluted 2 fold in initial UPLC conditions before analysis.

Separation is performed at +30° C. on a Waters ACQUITY UPLC BEH C18 1.7 μm, 2.1×50 mm, 130 Å column (W11) using UPLC apparatus with UPLC TUV detector and a Waters ACQUITY H-CLASS module. Data is acquired and is processed using Empower®3 software. The method is 30-028-02_UPLC_Imp with a run time of 5.5 min. Under these conditions, olanzapine is eluted at 1.34 min.

Example 4

In Vitro Release Profiles of Olanzapine Formulations

The in vitro release in tocophersolan modified, human plasma of four sustained release olanzapine formulations of the disclosure were carried out and compared to that of the commercially available long acting IM depot preparation containing olanzapine pamoate (ZALPREXA RELPREVV) using the procedures as set forth in Example 2.

Formulations were prepared according to published methodologies targeting a final API content of 30 mg and released slowly over 3-5 seconds into a media of plasma and tocophersolan. Sampling was performed at T=1, 2, 3, 4, 6, 24, 48 and 72 hours by UPLC. The remaining plasma was discarded and refreshed. Subsequently the samples were sealed, protected from light and incubated at +37° C. under constant agitation until the next time point.

The percentage of olanzapine released over time from the five formulations is depicted in FIG. 1.

The figure shows that the sustained release formulations show no signs of an initial burst, with a gradual release of olanzapine. This is in stark contrast to the release profile/dissolution profile for the olanzapine pamoate product, which exhibits a large burst with 50% of the total API being released into the plasma within the first hour. Subsequently, the reference product continues to dissolve until most of the olanzapine is available within 4-6 hours. Analysis of subsequent time points suggests a slow and linear increase in olanzapine dissolution until almost 100% is dissolved after 3 days. In comparison, at the one-hour time-point, the four sustained release formulations have released only approximately 1% of their total olanzapine content, 2% after 2 hours, 3% after 6 hours and only 15-20% after 1 day.

Example 5

In Vivo Release Profiles

Figure 2:
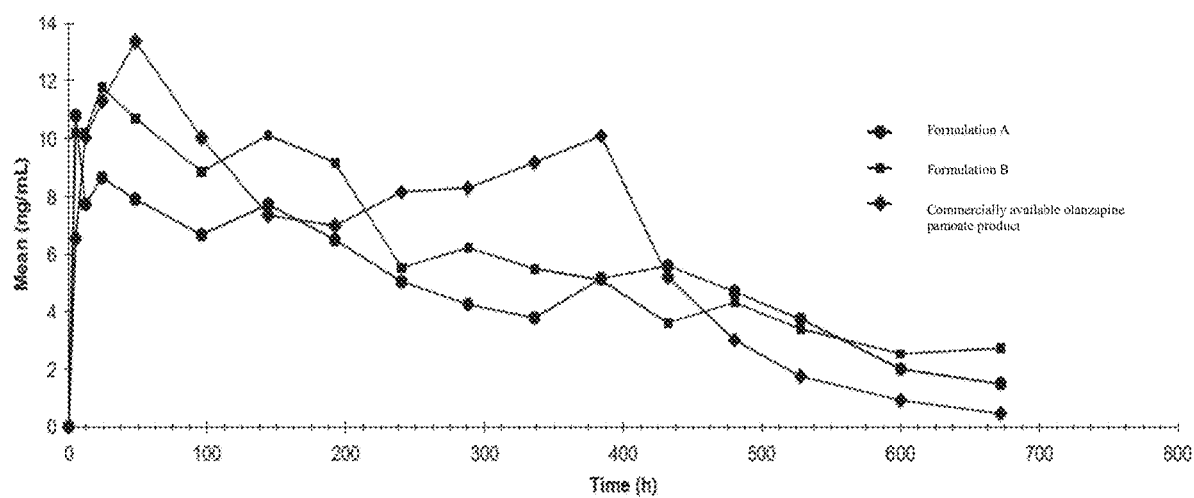
FIG. 2—is a graph that demonstrates the pharmacokinetic profiles in dogs following subcutaneous administration of the sustained release olanzapine formulations and IM administration of olanzapine pamoate.

Two sustained release olanzapine formulations of the disclosure were administered by subcutaneous (SC) injection as a single dose to 4 female Beagle dogs per dose group at a target dose of 10 mg/kg. The reference, olanzapine pamoate (ZALPREXA RELPREVV), was injected as a single dose of 10 mg/kg by IM route to another set of 4 female Beagle dogs. Blood samples were collected over a period of 29 days postdose. Clinical observations and local tolerance were performed during the course of the study. The pharmacokinetic profiles in dogs following subcutaneous administration of the two sustained release olanzapine formulations and IM administration of olanzapine pamoate are presented in FIG. 2.

The dog pharmacokinetic study concentration-time profile of olanzapine from the two sustained release olanzapine SC formulations in dogs, administered by the subcutaneous route at the dose of 10 mg/kg, indicated rapid absorption following subcutaneous administration with a low initial burst, as evidenced by a mean $C_{max}$ of 11.0 and 11.9 ng/mL, compared to 16.5 ng/mL for olanzapine pamoate. The absorption phase was followed by a slow-elimination phase that was consistent with a 1 month release. The mean total exposures (total area under the plasma drug concentration time curve) of olanzapine were 3967 and 5013 ng·h/mL, compared to 4339 ng·h/mL for olanzapine pamoate. These results indicate that the mean exposure of olanzapine and mean peak plasma level sustained release olanzapine formulations at 10 mg/kg were comparable to the exposure and peak plasma levels observed for olanzapine pamoate administered IM at 10 mg/kg. These data further indicate the safe and efficacious release profile of the formulations disclosed herein and the absence of detrimental peak-to-trough fluctuation.

Example 6

Open label 12 month safety study of approximately 350 patients.

Patients diagnosed with schizophrenia and/or bipolar disorder will receive subcutaneous injections of a formulation of the disclosure, once per month. Per-patient risk of olanzapine-induced PDSS will be less than that observed with ZYPREXA RELPREVV, i.e., less than a 1.4% risk.

The study will establish that the formulations of the disclosure, administered subcutaneously, are inherently safer than the IM formulation ZYPREXA RELPREVV, with regard to PDSS. Following preclinical studies, a human Phase 1 single and multiple ascending dose study will be conducted in approximately 90 schizophrenic patients. The inpatient SAD/MAD study will confirm that the formulations of the disclosure will sustain blood levels above a Cmin of 7-10 ng/ml for 1 month without exceeding 40 ng/ml $C_{max\ avg}$. A cutoff olanzapine blood level value will be determined. For example, the formulations of the disclosure will not produce olanzapine blood levels above 100 ng/ml in any single individual.

In addition to analyzing blood concentrations, signs of delirium, confusion, sedation, and the like will be monitored throughout the first 3 hours, i.e., for the period of time within which almost all cases of PDSS have been observed to occur. For example, the PDSS criteria outlined below will be used (see, e.g., Bushe et al. BMC Psychiatry (2015) 15:65, the entirety of which is incorporated by reference herein) or similar and clinically accepted criteria will be used.

1. One or both of the conditions listed in (a) and (b):
   (a) A minimum of one (1) sign or symptom from at least three (3) of the following symptom clusters consistent with olanzapine overdose with one or more of at least moderate severity:
   Sedation/somnolence
   Delirium/confusion/disorientation/other cognitive impairment
   Dysarthria/other speech impairment
   Ataxia/other motor impairment
   Extrapyramidal symptoms
   Agitation/irritability/anxiety/restlessness
   Dizziness/weakness/general malaise
   Seizure
   (b) Any one (1) of the following signs and symptoms:
   Unarousable
   Unconscious
   Stuporous
   Comatose
2. Condition develops within 24 hours of an olanzapine administration via injection.
3. Condition cannot be explained by a significant dose increase of injected olanzapine, initiation or addition of oral olanzapine or other sedating medication, or new exposure to injected olanzapine.
4. Underlying medical conditions have been ruled out, including concomitant substance use or abuse.
5. Olanzapine plasma level is >100 ng/mL≤3 hours after injection.

Statistically, a 0% risk of PDSS is challenging to establish. However, by giving a sufficient number of injections to a sufficient number of patients, it can be statistically demonstrated that a subcutaneously administered formulation of the disclosure has a lower incidence of PDSS as compared to the IM formulation ZYPREXA RELPREVV. For example, if the rate of PDSS for the IM formulation is 1.4% of patients, a statistically superior rate for the formulations of the disclosure can be established if the subcutaneous formulation is administered to the following number of patients and there is no event of PDSS.

For example, a formulation of the disclosure is administered to 526 patients and there is no PDSS event, the rate is 0.7% or less, or twice as good as the 1.4% rate reported for the IM formulation.

| Percent of Patients | Sample size** |
|---|---|
| 0.30% | 1231 |
| 0.40% | 921 |
| 0.50% | 736 |
| 0.60% | 613 |
| 0.70% | 526 |
| 0.80% | 460 |
| 0.90% | 409 |
| 1.00% | 368 |
| 1.10% | 334 |
| 1.20% | 306 |
| 1.30% | 282 |
| 1.40% | 262 |

**Power of 80%, drug PDSS rate of 0.000001, i-sided alpha of 0.025 using exact test Likewise, to demonstrate that the incidence of PDSS per injection is 0.03% compared to the known rate of the IM formulation (0.07%), 0 events in 10000 injections or 834 patients injected once a month for 12 months would need to be found, as shown in Table 3, below.

TABLE 3

| Standard PDSS Rate Percent of Injection | Number of Injections | Sample size (number of injection/12) |
|---|---|---|
| 0.01% | 30000 | 2500 |
| 0.02% | 15000 | 1250 |
| 0.03% | 10000 | 834 |
| 0.04% | 7500 | 625 |
| 0.05% | 6000 | 500 |
| 0.06% | 5000 | 417 |
| 0.07% | 4286 | 358 |

The invention claimed is:

1. A method of treating schizophrenia or bipolar disorder in a patient comprising:
   subcutaneously administering to the patient, with a frequency of no more than once per 21 days, a sustained-release pharmaceutical dosage form comprising olanzapine, or a pharmaceutically acceptable salt thereof;
   wherein the dosage form provides a therapeutically effective dose of olanzapine for a period of at least 21 days;
   wherein the upper limit of a 95% Confidence Interval for the $C_{max,\ avg}$ is ≤100 ng/ml; and
   wherein said method is performed without monitoring for post-injection delirium/sedation syndrome (PDSS).

2. The method of claim 1, wherein the pharmaceutical dosage form comprises olanzapine.

3. The method of claim 1, wherein the pharmaceutical dosage form comprises a pharmaceutically acceptable olanzapine salt.

4. The method of claim 1, wherein the pharmaceutical dosage form comprises between about 150 mg and about 900 mg of olanzapine or a pharmaceutically acceptable salt thereof.

5. The method of claim 4, wherein the pharmaceutical dosage form comprises between about 300 mg and about 600 mg of olanzapine or a pharmaceutically acceptable salt thereof.

6. The method of claim 4, wherein the pharmaceutical dosage form comprises about 300 mg of olanzapine or a pharmaceutically acceptable salt thereof.

7. The method of claim 4, wherein the pharmaceutical dosage form comprises about 405 mg olanzapine or a pharmaceutically acceptable salt thereof.

8. The method of claim 4, wherein the pharmaceutical dosage form comprises about 600 mg olanzapine or a pharmaceutically acceptable salt thereof.

9. The method of claim 1, wherein the pharmaceutical dosage form further comprises at least one biodegradable polymer.

10. The method of claim 9, wherein the at least one biodegradable polymer is a poly(lactide), poly(glycolide), poly(lactide-co-glycolide), poly-l-lactic acid, poly-d-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), poly(amino acid), polyesteramide, polyanhydrides, polyphosphazines, poly(alkylene alkylate), biodegradable polyurethane, polyvinylpyrrolidone, polyalkanoic acid, polyethylene glycol, copolymer of polyethylene glycol and polyorthoester, albumin, chitosan, casein, waxes or blends or copolymers thereof.

11. The method of claim 1, wherein the pharmaceutical dosage form provides a therapeutically effective dose of olanzapine for a period of at least about 30 days.

12. The method of claim 11, wherein the pharmaceutical dosage form provides a therapeutically effective dose of olanzapine for a period of at least about 60 days.

13. The method of claim 11, wherein the pharmaceutical dosage form provides a therapeutically effective dose of olanzapine for a period of about 90 days.

14. The method of claim 1, wherein the pharmaceutical dosage form provides an upper limit of a 95% Confidence Interval for the $C_{max,\ avg}$ that is ≤90 ng/ml.

15. The method of claim 14, wherein the pharmaceutical dosage form provides an upper limit of a 95% Confidence Interval for the $C_{max,\ avg}$ that is ≤80 ng/ml.

16. The method of claim 15, wherein the pharmaceutical dosage form provides an upper limit of a 95% Confidence Interval for the $C_{max,\ avg}$ that is ≤70 ng/ml.

17. The method of claim 16, wherein the pharmaceutical dosage form provides an upper limit of a 95% Confidence Interval for the $C_{max,\ avg}$ that is ≤60 ng/ml.

18. The method of claim 17, wherein the pharmaceutical dosage form provides an upper limit of a 95% Confidence Interval for the $C_{max,\ avg}$ that is ≤50 ng/ml.

19. The method of claim 1, wherein the pharmaceutical dosage form provides a $C_{max,\ ind}$ of ≤100 ng/ml.

20. The method of claim 19, wherein the pharmaceutical dosage form provides a $C_{max,\ ind}$ of ≤90 ng/ml.

21. The method of claim 20, wherein the pharmaceutical dosage form provides a $C_{max,\ ind}$ of ≤80 ng/ml.

22. The method of claim 21, wherein the pharmaceutical dosage form provides a $C_{max,\ ind}$ of ≤70 ng/ml.

23. A method of administering between about 150 mg and about 900 mg of olanzapine, or a pharmaceutically acceptable salt thereof, to a patient comprising: subcutaneously administering to the patient a sustained-release olanzapine pharmaceutical dosage form at a frequency of no more than once per 21 days and provides an upper limit of a 95% Confidence Interval for the $C_{max,\ avg}$ that is ≤100 ng/ml;
   wherein the per-injection risk of PDSS being observed in the patient following the administration is less than 0.07% and/or the per-patient risk of PDSS being observed in the patient following the administration is less than 1.4%.

24. The method of claim 23, wherein the frequency of administration is no more than once per month.

25. The method of claim 24, wherein the frequency of administration is no more than once every two months.

26. The method of claim 23, wherein the pharmaceutical dosage form comprises between about 300 mg and about 600 mg of olanzapine or a pharmaceutically acceptable salt thereof.

27. The method of claim 26, wherein the pharmaceutical dosage form comprises about 300 mg of olanzapine or a pharmaceutically acceptable salt thereof that is equivalent to about 300 mg of olanzapine.

28. The method of claim 26, wherein the pharmaceutical dosage form comprises about 405 mg olanzapine or a pharmaceutically acceptable salt thereof that is equivalent to about 405 mg of olanzapine.

29. The method of claim 26, wherein the pharmaceutical dosage form comprises about 600 mg olanzapine or a pharmaceutically acceptable salt thereof that is equivalent to about 600 mg of olanzapine.

30. The method of claim 23, wherein the pharmaceutical dosage form further comprises at least one biodegradable polymer.

31. The method of claim 30, wherein the at least one biodegradable polymer is a poly(lactide), poly(glycolide), poly(lactide-co-glycolide), poly-l-lactic acid, poly-d-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), poly(amino acid), polyesteramide, polyanhydrides, polyphosphazines, poly(alkylene alkylate), biodegradable polyurethane, polyvinylpyrrolidone, polyalkanoic acid, polyethylene glycol, copolymer of polyethylene glycol and polyorthoester, albumin, chitosan, casein, waxes or blends or copolymers thereof.

32. The method of claim 23, wherein the pharmaceutical dosage form provides a therapeutically effective dose of olanzapine for a period of at least about 30 days.

33. The method of claim 32, wherein the pharmaceutical dosage form provides a therapeutically effective dose of olanzapine for a period of at least about 60 days.

34. The method of claim 33, wherein the pharmaceutical dosage form provides a therapeutically effective dose of olanzapine for a period of about 90 days.

35. The method of claim 23, wherein the pharmaceutical dosage form provides an upper limit of a 95% Confidence Interval for the $C_{max,\ avg}$ that is ≤90 ng/ml.

36. The method of claim 35, wherein the pharmaceutical dosage form provides an upper limit of a 95% Confidence Interval for the $C_{max,\ avg}$ that is ≤80 ng/ml.

37. The method of claim 36, wherein the pharmaceutical dosage form provides an upper limit of a 95% Confidence Interval for the $C_{max,\ avg}$ that is ≤70 ng/ml.

38. The method of claim 37, wherein the pharmaceutical dosage form provides an upper limit of a 95% Confidence Interval for the $C_{max,\ avg}$ that is ≤60 ng/ml.

39. The method of claim 38, wherein the pharmaceutical dosage form provides an upper limit of a 95% Confidence Interval for the $C_{max,\ avg}$ that is ≤50 ng/ml.

40. The method of claim 35, wherein the pharmaceutical dosage form provides a $C_{max,\ ind}$ of ≤100 ng/ml.

41. The method of claim 40, wherein the pharmaceutical dosage form provides a $C_{max,\ ind}$ of ≤90 ng/ml.

42. The method of claim 41, wherein the pharmaceutical dosage form provides a $C_{max,\ ind}$ of ≤80 ng/ml.

43. The method of claim 42, wherein the pharmaceutical dosage form provides a $C_{max,\ ind}$ of ≤70 ng/ml.

44. The method of claim 23, wherein the per-injection risk of PDSS being observed in the patient following the administration is less than 0.01%.

45. The method of claim 44, wherein the per-injection risk of PDSS being observed in the patient following the administration is less than 0.005%.

46. The method of claim 45, wherein the per-injection risk of PDSS being observed in the patient following the administration is less than 0.001%.

47. The method of claim 46, wherein the per-injection risk of PDSS being observed in the patient following the administration is less than 0.0005%.

48. The method of claim 23, wherein the per-injection risk of PDSS being observed in the patient following the administration is 0%.

49. The method of claim 23, wherein the per-patient risk of PDSS being observed in the patient is less than 1.4%.

50. The method of claim 49, wherein the per-patient risk of PDSS being observed in the patient is less than 1%.

51. The method of claim 50, wherein the per-patient risk of PDSS being observed in the patient is less than 0.75%.

52. The method of claim 51, wherein the per-patient risk of PDSS being observed in the patient is less than 0.5%.

53. The method of claim 52, wherein the per-patient risk of PDSS being observed in the patient is less than 0.25%.

54. The method of claim 53, wherein the per-patient risk of PDSS being observed in the patient is less than 0.1%.

55. The method of claim 54, wherein the per-patient risk of PDSS being observed in the patient is less than 0.05%.

56. The method of claim 55, wherein the per-patient risk of PDSS being observed in the patient is 0%.

57. The method of claim 23, wherein the patient has been diagnosed with schizophrenia.

58. The method of claim 23, wherein the patient has been diagnosed with bipolar disorder.

* * * * *